United States Patent [19]

Wenz et al.

[11] 4,202,665

[45] May 13, 1980

[54] DETECTION OF HEPATITIS B SURFACE ANTIGEN

[75] Inventors: Barry Wenz, White Plains; Arthur Karmen, Manhasset; Chi Shun Feng, Yonkers, all of N.Y.

[73] Assignee: Albert Einstein College of Medicine of Yeshiva University a Division of Yeshiva University, Bronx, N.Y.

[21] Appl. No.: 957,749

[22] Filed: Nov. 6, 1978

[51] Int. Cl.² ............................................. G01N 33/16
[52] U.S. Cl. .................................... 23/230 B; 424/12
[58] Field of Search ................... 424/12, 72; 23/230 B

[56] References Cited

U.S. PATENT DOCUMENTS

| | | | |
|---|---|---|---|
| 3,829,223 | 8/1974 | Hamel | 422/72 X |
| 3,992,517 | 11/1976 | Lowke | 424/12 |
| 4,080,264 | 3/1978 | Cohen | 424/12 X |
| 4,113,712 | 9/1978 | Fundroshi | 424/12 X |
| 4,130,634 | 12/1978 | Molinaro | 424/12 X |
| 4,133,873 | 1/1979 | Noller | 424/12 X |
| 4,136,161 | 1/1979 | Falkowski | 424/12 X |

Primary Examiner—Sidney Marantz
Attorney, Agent, or Firm—Stephen E. Feldman; Marvin Feldman

[57] ABSTRACT

The reversed passive hemagglutination test (RPHA) for the detection of hepatitis B surface antigen ($HB_sAg$) is improved by the recognition that the speed of movement towards the periphery of a centrifugal field by immunologically aggregated solid phase support particles, increases proportionally with the amount of antigen present. It is further recognized that this dynamic study can be performed objectively and in an automated fashion by equipment such as the miniature centrifugal fast analyzer. The test performed in this manner and known as "reversed passive hemagglutination by minature centrifugal fast analysis" (RPHA/MCFA) is highly specific and eliminates the need for subsequent confirmational studies. Preliminary studies confirm a sensitivity comparable to other third generation tests.

28 Claims, 4 Drawing Figures

DETECTION OF HEPATITIS B SURFACE ANTIGEN

BACKGROUND AND FIELD OF USE

This invention relates to the immunological detection of hepatitis virus particles in blood. Specifically this invention relates to a modification of the reversed passive hemagglutination technique for the detection of hepatitis B surface antigen (HBsAg) with the use of automated equipment, such the miniature centrifugal fast analyzer.

DISCUSSION OF THE PRIOR ART

Many tests have been developed and used to detect the presence of hepatitis B surface antigen in body fluids. The first generation of tests which were developed, such as the agar-gel diffusion and complement fixation tests, do not display sufficient sensitivity to detect small quantities of antigen. This is a serious failing, since blood tested as negative for $HB_SAg$ by these methods, could possibly transmit serum hepatitis to a recipient. Actually the hepatitis antigen is present in such infective blood but at very low levels of concentration, beyond the detection capabilities of these tests.

Subsequently developed test procedures are more sensitive and can detect antigen concentrations comparable to 2.5 nanograms of protein per milliliter, however, these tests also have serious shortcomings. In the manuscript "Radioimmunoassay of Australia Antigen", published by Walsh, Yalow and Berson (Vox Sang. 19:217, 1970), the radioimmunoassay (RIA) detection procedure is described. By using immunological principles, antigen is quantitatively detected through its reactivity with a radioactively labeled antibody. This test results in an objective measurement, however, the reaction of the heterologous radioactively labeled protein with naturally occuring human anti-species antibodies can and does result in false positive reactions. In such instances, the test indicates the presence of the hepatitis antigen when it is not actually present, but merely mimicked by the non-specific and undesirable reaction described above.

In another article, "Hemagglutination Technique with Erythrocytes Coated with Specific Antibody for Detection of Australia Antigen" published by T. Juji and T. Yokodi, *Jap. J. Exp. Med.* 39:615, 1969), it is shown that the hepatitis B surface antigen can be detected by observation of the sedimentation patterns created by the reaction between the specimen (i.e. serum) and a prepared reagent red cell button. The presence or absence of the hepatitis B surface antigen is subjectively determined by the degree of the sedimentation achieved by the reagent red cells which are coated with antibodies to the hepatitis B surface antigen (Anti-$HB_S$). The test does not quantify the amount of antigen present and is adversely influenced by false positive results. Failure to achieve complete sedimentation may not in fact be due to the reaction of the antibody with the hepatitis B Surface antigen, as in the RIA study.

The two previously discussed procedures (RIA, RPHA) are currently the most extensively used tests for the detection of the hepatitis B surface antigen. Yet since the fallibility of these tests is known, it is often necessary to run a time consuming and expensive second set of tests to confirm positive results.

This present invention recognizes that the reaction which occurs between the hepatitis B surface antigen and its antibody occurs at a rate which is novel and unlike the reaction rate of the reactions which produce false positive results. It has been found that by dynamically measuring the rate of movement of complexes formed by reactions between the hepatitis B surface antigens, and the antibodies present on the reagent red cells used in the RPHA Test, the presence of hepatitis B surface antigen can be determined in an accurate and specific fashion. Furthermore, by use of the described automated procedure (viz: The RPHA/MCFA=Reversed Passive Hemagglutination by Miniature Centrifugal Fast Analysis) the results are obtained quickly, objectively and in a quantitative manner. Most importantly this MCFA-RPHA test obviates the need for confirmatory testing.

An object of this invention is therefore to provide a novel method for the detection of hepatitis B surface antigen.

Another object of this invention is to provide a method for the detection of hepatitis B surface antigen as aforesaid wherein the detection is achieved by use of a miniature centrifugal fast analyzer.

A further object of this invention is to provide a method for the detection of hepatitis B surface antigen as aforesaid wherein the need for confirmatory testing is eliminated.

It is another aspect of this invention to provide a method for the detection of hepatitis B surface antigen as aforesaid wherein the detection is automatic and objective.

It is a further aspect of this invention to provide a method for the detection of hepatitis B surface antigen as aforesaid wherein the results are specific and quantitative.

It is another aspect of this invention to provide a method for the detection of hepatitis B surface antigen as aforesaid wherein the results are obtained from a single testing procedure.

It is a further aspect of this invention to provide a method for the detection of hepatitis B surface antigen as aforesaid where the need for radioactive material is eliminated.

It is a further aspect of this invention to extend these specifications and methodologies to all immunological testing using antigen (or antibody) which is bound to a solid phase support for the detection and/or quantification of its respective antibody (or antigen).

The aforesaid as well as other objects and advantages of the present invention will become apparent from a reading of the following specifications, the adjoined claims; and the drawings in which:

DISCUSSION OF THE PREFERRED EMBODIMENT

Figure 1:
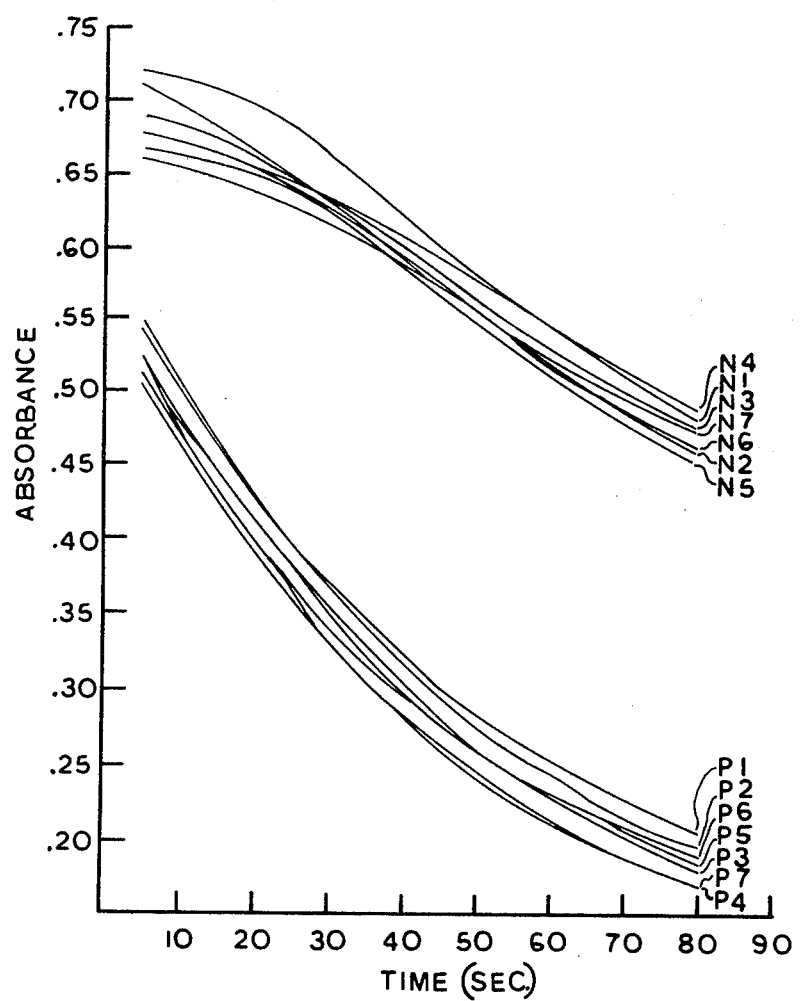
FIG. 1 is a graph of absorbance values vs. time for several positive (P) and negative (N) standards.

Broadly speaking, one preferred embodiment of the present invention is the detection of hepatitis B surface antigen in blood through the use of centrifugal analyzers such as the miniature centrifugal fast analyzer (MCFA). Specifically, a preferred embodiment involves use of a reversed passive hemagglutination test which operates on the principle that antigens and their corresponding antibodies which are coated on to solid phase supports, will initiate an agglutination reaction when they are simultaneously present. An observer can therefore determine from the reaction product formed, whether or not the corresponding antigen is present in an analyzed specimen. It is discovered in this invention that the rate of movement of the solid phase support (i.e. red cells) which is coupled to antibody (i.e. Anti $HB_s$), can be monitored in a centrifugal field by a centrifugal analyzer. It is further discovered that by measuring the speed of such movement, with recognition of other factors to be more fully discussed hereinafter, the presence and the amount of hepatitis B surface antigen in a specimen can be determined. Without being bound to any particular theory or mechanism, it is believed that the problem of "false positives" is eliminated because agglutination caused by the reaction between the antibody and an antigen other than $HB_sAg$ occurs at a rate different than the rate of agglutination which occurs between the hepatitis B surface antigen and its antibody.

The general procedure in using an MCFA as well as the principles benind its operation have been previously published by Tiffany, T. O., Burtis, C. A., Maden, L. C., and Tacker, L. E., in an article entitled "Dynamic Multicuvette Flurometer—Spectrophotometer Based on the GeMSAeC Fast Analyzer Principle," *Anal. Chem.*, 45;1716, 1973.

It is of course to be understood that in the broad aspect of this invention the centrifugal analysis may be made by apparatus other than the MCFA. Such technology should incorporate the mixing and transfer of the specimens and the reagents by centrifugation, and the concomitant and dynamic measurement of the reaction mixture by spectrophotometric principles.

Without intending to limit this invention in any respect, a mini-GeMSAeC, model #25004, manufactured by Oak Ridge National Laboratory, was used to attain the experimental results which follow. An MCFA is essentially a spectrophotometric detection device which employs centrifugal force to transfer reaction mixtures to cuvettes, where they are sequentially monitored. The aforesaid particular model consists of a rotor with 17 cuvettes which are equally positioned about the circumference. Each cuvette is feed by 2 wells which are positioned along its radius and are connected to it by channels. The wells comprise loading reservoirs for reagents and specimens, respectively. The reactions which occur in the cuvettes are monitored by a spectrophotometer and recorded by a computer and teletype printer.

The reversed passive hemagglutination test was performed using the RPHA kit for the detection of hepatitis B surface antigen marketed under the name Auscell (a product of Abbott Laboratories). The materials contained in the kit are:

(a) Duracytes—lyophilized human red cells coupled to guinea pig antibody to hepatitis B surface antigen (Anti-HBs)

(b) Reconstitution Solution—0.08 M phosphate buffer (pH. 7.2), which is used to reconstitute the Duracytes;

(c) Specimen Dilution Buffer—0.1 M phosphate buffer (pH 7.2) containing gelatin, guinea pig serum and recalcified normal human plasma;

(d) a positive control which is diluted HBsAg positive human serum.

The foregoing equipment and materials were used to conduct the experiments for detection and quantification of hepatitis B surface antigen in human sera. A battery of tests were performed to determine the following parameters: the rate of reaction of HBsAg with anti HBs in saline and in specimen dilution buffer; the incubation time of the reaction between the HBsAg with anti HBs and lastly, the concentration of the HBsAg present. However, the broad principles of this reaction are applicable to other manufacturers' reagents and may be employed to measure antigens or antibodies other than those concerned with hepatitis.

EXPERIMENTAL EXAMPLE 1

The Duracytes, of composition heretofore described, were combined with the reconstitution solution as specified by the kit manufacturer's instructions. The reconstituted Dyracytes were then placed in the MCFA's automatic loading station which was programmed to supply 60 $\mu$l of the Duracyte suspension to the reagent wells.

The control and test sera were each mixed with 7 volumes of specimen dilution buffer. These diluted test sera solution was also placed in the MCFA's automatic loading station which was instructed to feed 40 $\mu$l of these sera to each specimen well. In addition, as directed by published articles on the use of a MCFA, a 15 $\mu$l "flush" of physiological saline was incorporated into the "loading" sequence, in order to rinse all test sera out of the pipettes and to avoid "carry-over" during sequential analyses.

After the foregoing "loading" is performed, the rotor is centrifuged to a speed of 4000 RPM and once this speed is achieved, the rotor is immediately braked to a full stop. This maneuver transfers the contents of the specimen and reagent wells to the peripheral cuvettes. The rotor is then allowed to remain at rest, at room temperature for 30 minutes. The rotor is then accelerated to 450 RPMs, and the absorbance readings for each cuvette are monitored and record for 90 seconds at 5 second intervals, at a wavelength of 415 nm. The rotor is then accelerated to 4000 RPM for 1 minute, allowed to decelerate to 450 RPM, at which time a second series of readings are taken at 5 second intervals at 415 nm. The purpose of the second reading is to compensate for background absorption caused by nonstandardized pigmentation of the sera. The high speed rotation removes all the particulate matter from the light path and allows for an absorbance reading due solely to the pigmentation. When this second reading is subtracted from the results of the primary readings, the resultant values reflect the rate of change in the absorption of the antibody containing red cells alone. It is thereby determined that the rate of change in the absorption (i.e. movement from the light path) of the antibody containing red cells in the presence of a standardized HBsAg positive serum is approximately three times greater than the rate of change in the absorption of these cells in the absence of the antigen (i.e. negative standard.)

The following is a set of comparative studies where cuvette 1 contains the negative standard and cuvette 2 contains the positive standard:

|  | Time (Sec) | Cuvette 1 | Cuvette 2 |
|---|---|---|---|
| Reading 1 | | | |
| (Dynamic | 5 | 1.1207 | 0.5051 |
| absorbance | 10 | 1.1229 | 0.4478 |
| change) | 15 | 1.1213 | 0.3825 |
| Reading 2 | 5 | 0.4623 | 0.0891 |
| (adjustment | 10 | 0.4623 | 0.0893 |
| for pigmentemia) | 15 | 0.4622 | 0.0892 |

FIG. 1 (appended) contrasts the rate of change in absorbance between positive and negative control sera which are included in the manufacturer's Kit. As displayed in the Figure, the mean rate of change in absorbance (slope) for 7 negative controls is 0.14±0.04 and the mean rate change in absorbance for 7 positive controls is 0.43±0.03. These data further confirm the consistency of the three-fold differences between standards.

EXPERIMENTAL EXAMPLE 2

The same procedure was employed as in Example 1 with the sole difference being that the test sera was diluted with saline rather than the dilution buffer.

Figure 2:
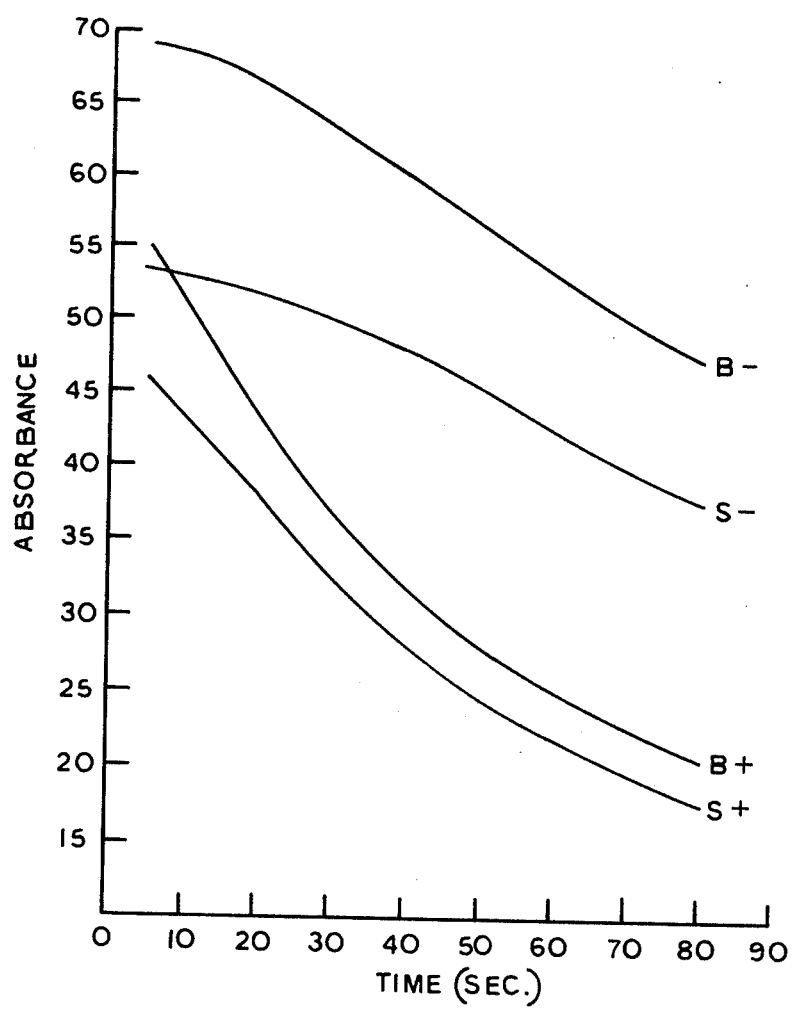
FIG. 2 is a graph of absorbance values vs. time for positive (B+) and negative (B−) standards performed in specific buffered media and for the positive (S+) and negative (S−) standards performed in physiological.

FIG. 2 represents the readings taken of the same positive and negative standards as in FIG. 1, which were alternatively suspended in buffer (B+/B−) or in Saline (S+/S−). The rate change (dy/dx) of the individual standards are as follows: B−, 0.13; S−, 0.10; B+, 0.40; S+, 0.32.

This example demonstrates that the difference between the rates of change of the negative and positive standards remained three times as great even with the change of dilution solution, and accordingly is a function which is independent of the suspending medium. Saline or other media can therefore also be used to dilute the test sera in this MCFA/RPHA test procedure. This ability to substitute dilution media contrasts sharply with the sedimentation requirements of the conventional (Auscell) RPHA test.

EXPERIMENTAL EXAMPLE 3

Figure 3:
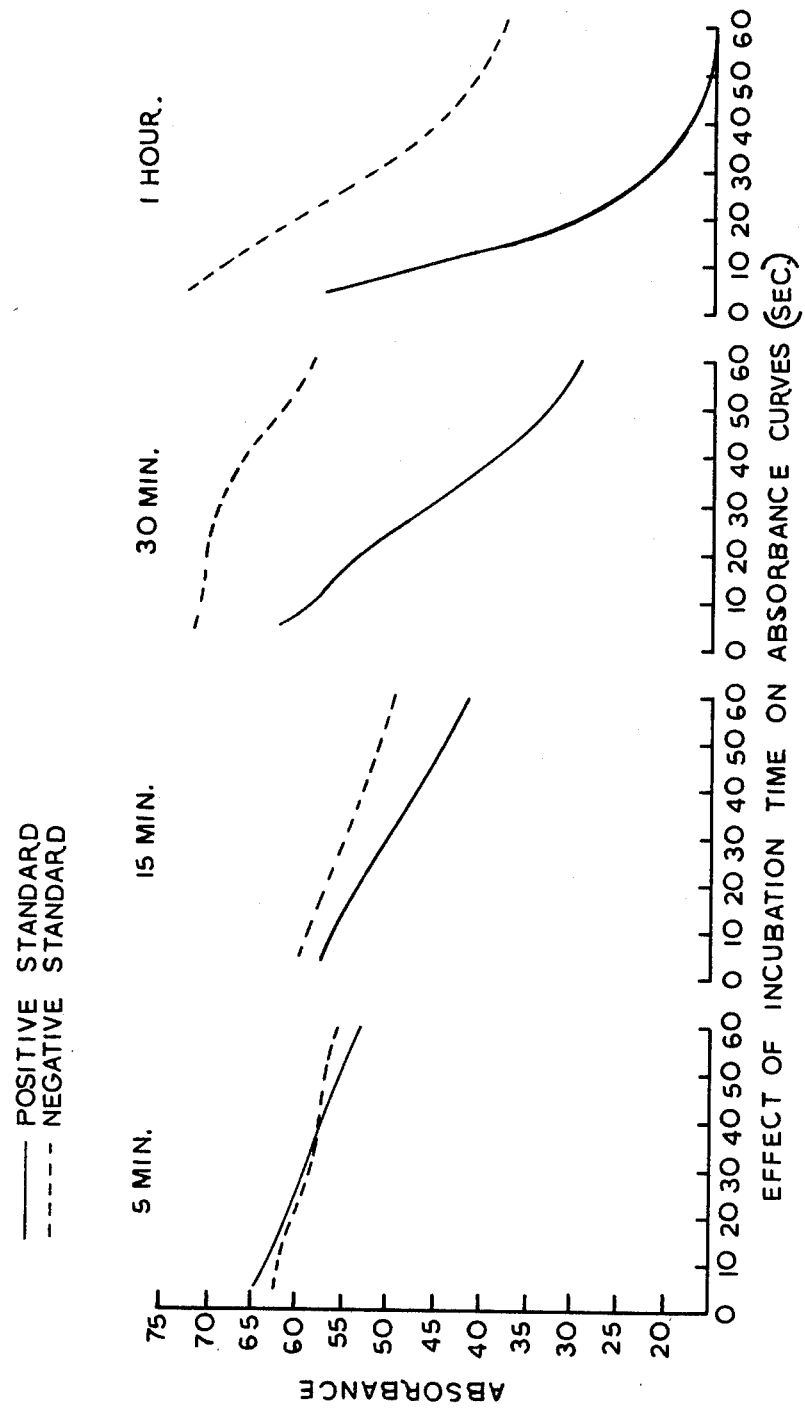
FIG. 3 is four sequential graphs showing absorbance vs. time, for different incubation periods.

The same procedure was followed as used in Example 1 except that the rotor was allowed to remain at rest for periods varying from 5 minutes to 2 hours. Readings were subsequently taken in the exact same manner as in Example 1. The results are indicated in FIG. 3 with the solid lines representing the positive standards and the dotted lines representing the negative standards.

This example demonstrates that the time allowed for incubation of the serum and Duracyte mixtures does affect the resultant rate of change in absorbance of these standards. The difference between the negative and positive standards' rate of change is maximum after 30 minutes. It is also during this period of time, i.e. 30 minutes, that the undue influence exerted by serological factors which cause "false positive" results in conventional tests, is excluded. It is further noted that although this 30 minute incubation period results in dramatic differences between positive and negative sera, discrimination is possible during various incubation periods ranging from 1 minute to more than 8 hours.

EXPERIMENTAL EXAMPLE 4

Figure 4:
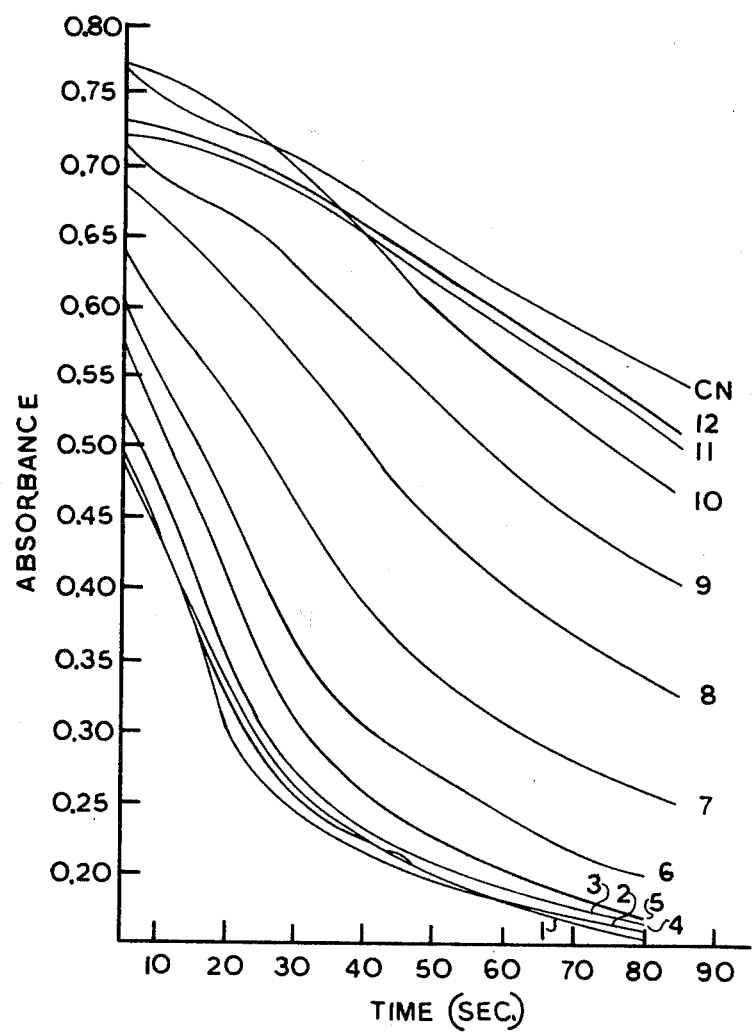
FIG. 4 is a graph of absorbance vs. time for various dilutions of antigen.

The same procedure was followed as in Example 1 except that the concentration of the hepatitis B surface antigen was varied by serial two-fold dilution of a positive specimen. FIG. 4, with curves 1-12, represents dilution of native serum ranging from 1:64 (curve 1) to $1:1.3 \times 10^5$ (curve 12). The top line CN is a negative standard employed as a reference.

This example demonstrates that the rate of change in absorbance decreases with each successive dilution of the test specimen in a predictable and quantitative fashion. This example also demonstrates the sensitivity of the MCFA-RPHA test procedure which can detect HBsAg at dilutions less than $1:6.5 \times 10^4$, comparable to the conventional RPHA test.

While the aforesaid discussion has been directed towards analysis of human blood, this invention could also be used detect hepatitis B surface antigen in the sera of other animals, particularly the higher animals sharing many features and traits with man. This invention can also detect hepatitis in materials other than blood. In point of fact, this invention can be used to detect other antigens or antibodies as well, including by way of example, the antibody to German measles (rubella virus).

It is also to be understood that although the intent of the foregoing is for the detection of hepatitis particles, particularly in blood for the determination of its suitability for transfusions, this invention may also be used as a method for the diagnosis of hepatitis.

This invention is also not limited to the particular model centrifugal analyzer used or to the Auscell RPHA kit. Any centrifugal analyzer, RPHA or PHA kit may be used that would be regarded as acceptable by an expert in the field.

Although the preferred incubation time is approximately 30 minutes, incubation may vary from 1 minute to 500 minutes.

It is also to be understood that although the specimen dilution solutions include saline and phosphate buffer solutions it is within the scope of the present invention to use other solutions that an expert in the field would recognize as capable of achieving the desired result. The reconstitution formula may also be varied to include other than phosphate buffer solutions.

Although the preferred embodiment of this invention includes an acceleration of 450 to 4000 RPM, it is within the contemplation of this invention that acceleration may vary from 200 to 7000 RPM.

Although standard temperature and pressure were employed in the preferred embodiment, this invention may be practiced at temperatures from about 0° to 37° C.

It is also understood that although the rate of change shown by the positive standard is 3 times as great as the negative standard, this invention also includes results where the rate of change is about 1.5 to 10 times as great.

In the practice of the present invention, the antibody or the antigen may be present on any suitable solid substrate. While the foregoing described a fluid specimen, such as the human blood, wherein the red blood cells would be the substrate for antigen activity, it is within the contemplation of the method of this invention to combine a solid substrate and antigen with antibodies and measure the rate of light absorbance of the antibody in the combined presence of the antigen on the substrate. Suitable substrates pursuant to the present invention include the biologicals, such as red blood cells (e.g. human, primate, avian) and the like, and non-biologicals including the organics, fine particulate substrates such as synthetic polymeric materials (e.g. polyolefins, latex elastomer, Sepharose and the like) and inorganics such as metal particulates (e.g. iron), carbon (e.g. charcoal) and the like. Thus this present invention is useful to any immunological system employing a solid phase support for the detection and or quantification of an antigen or antibody.

This invention is not limited to the specific examples which have been offered merely as illustrations. Modification may be made without departing from the spirit of the invention.

What is claimed is:

1. A method for the detection of hepatitis antigen in a fluid specimen comprising:
   (a) feeding a fluid reagent containing a solid support having an antibody and a specimen containing an antigen specific to the antibody to a centrifuge
   (b) accelerating the centrifuge to combine the specimen and the reagent; and
   (c) measuring the rate of change in light absorbance caused by the motion of the solid phase support in a centrifugal field.

2. The method of claim 1 wherein the hepatitis antigen is a hepatitis B surface antigen.

3. The method of claim 1 wherein the fluid is human blood, and the solid support is lyophilized human red blood cells.

4. The method of claim 3 further comprising incubating the combination of the blood specimen and the reagents from 1 minute to 500 minutes after acceleration.

5. The method of claim 4 wherein the hepatitis antigen is a hepatitis B surface antigen.

6. The method of claim 3 further comprising the acceleration and measuring of the rate of change in light absorbance of a positive and negative standard whereby the measurements are for comparison with the measurements of the combination of the blood specimen and reagent red cells.

7. The method of claim 6 wherein the acceleration of the positive and negative standards is simultaneous with the acceleration of the blood specimen and reagent red cells.

8. The method of claim 3 wherein measurements are taken from 0 secs. to 180 seconds after incubation at a constant acceleration from 100 RPMs to 4000 RPMs.

9. The method of claim 8 wherein measurements are taken at about 450 RPMs.

10. The method of claim 6 further comprising measuring the rate of change of the positive standard during the period of measurement which is a value approximately 3 times the rate of change of the negative standard whereby said value is for comparison with the measured value of the rate of change during the period of measurement of the blood specimen and reagent red cell combination.

11. The method of claim 3 further comprising diluting the blood specimen with a solution of pH 6 to pH 8 to an antigen concentration of $1:6.5 \times 10^4$ titers to 1:50 titers, prior to step a.

12. The method of claim 11 wherein the solution is a buffer solution.

13. The method of claim 11 wherein the solution is saline.

14. The method of claim 11 wherein an MCFA is used to accelerate and measure the rate of change in light absorbance of the combination of the fluid specimen and the reagent.

15. The method of claim 1 wherein the measured rate of change in light absorbance is recorded by a computer.

16. A method for the detection of an antigen comprising:
   (a) feeding a reagent comprising solid substrate particulates coated with antibody specific to the antigen, and a solution containing antigens to acceleration means;
   (b) accelerating to combine the specimen and antibody substrate suspension; and
   (c) measuring the rate of change in light absorbance of the substrate in the combined presence of the antibody on the substrate and the antigen in the medium.

17. The method of claim 16 wherein the solid substrate is a polymeric material.

18. The method of claim 16, wherein the solid substrate is a polyolefin.

19. The method of claim 16, wherein the solid substrate is an inorganic material.

20. The method of claim 16, wherein the solid substrate is in a fluid.

21. A method for the determination of immunological activity comprising:
   (a) feeding a reagent comprising a solid support material and an antigen and antibody specific to the antigen, to acceleration means;
   (b) accelerating the specimen; and
   (c) measuring the rate of change in light absorbance of the immunological activity.

22. The method of claim 21 wherein the specimen is in a fluid.

23. The method of claim 21, wherein at least one of the antibody or antigen is coupled to the solid support phase.

24. A method for the detection of an antibody comprising:
   (a) feeding a specimen comprising solid substrate particulates coated with antigen, and a solution containing antibody specific to the antigen, to acceleration means;
   (b) accelerating to combine the specimen and antigen substrate suspension; and
   (c) measuring the rate of change in light absorbance of the substrate in the combined presence of the antigen on the substrate and the antibody in the medium.

25. The method of claim 24, wherein the solid substrate is a polymeric material.

26. The method of claim 24, wherein the solid substrate is a polyolefin.

27. The method of claim 24, wherein the solid substrate is an inorganic material.

28. The method of claim 24, wherein the solid substrate is in a fluid.

* * * * *